(12) United States Patent
McFarland

(10) Patent No.: US 10,842,128 B2
(45) Date of Patent: Nov. 24, 2020

(54) METHOD AND APPARATUS FOR APPLYING, MONITORING, AND ADJUSTING A STIMULUS TO A PET

(71) Applicant: Radio Systems Corporation, Knoxville, TN (US)

(72) Inventor: Scott McFarland, Knoxville, TN (US)

(73) Assignee: RADIO SYSTEMS CORPORATION, Knoxville, TN (US)

( * ) Notice: Subject to any disclaimer, the term of this patent is extended or adjusted under 35 U.S.C. 154(b) by 363 days.

(21) Appl. No.: 15/839,749

(22) Filed: Dec. 12, 2017

(65) Prior Publication Data

US 2019/0174717 A1    Jun. 13, 2019

(51) Int. Cl.
| | | |
|---|---|---|
| *A01K 15/02* | (2006.01) | |
| *G01L 1/20* | (2006.01) | |
| *G05F 1/10* | (2006.01) | |
| *A01K 27/00* | (2006.01) | |
| *A61N 1/36* | (2006.01) | |

(52) U.S. Cl.
CPC ............. *A01K 15/021* (2013.01); *G01L 1/20* (2013.01); *G05F 1/10* (2013.01); *A01K 27/009* (2013.01); *A61N 1/36003* (2013.01)

(58) Field of Classification Search
CPC ...... A01K 15/021; A01K 27/009; G01L 1/20; G05F 1/10; A61N 1/36003
See application file for complete search history.

(56) References Cited

U.S. PATENT DOCUMENTS

| | | |
|---|---|---|
| 2,364,994 A | 12/1944 | Moore |
| 2,741,224 A | 4/1956 | Putnam |
| 3,182,211 A | 5/1965 | Maratuech et al. |

(Continued)

FOREIGN PATENT DOCUMENTS

| | | |
|---|---|---|
| CN | 101112181 A | 1/2008 |
| CN | 101937015 A | 1/2011 |

(Continued)

OTHER PUBLICATIONS

Eileen—How to Protect Your Dog From Loud and Scary Sounds (Year: 2013).

(Continued)

*Primary Examiner* — Amine Benlagsir
(74) *Attorney, Agent, or Firm* — Baker, Donelson, Bearman, Caldwell & Berkowitz PC

(57) ABSTRACT

A device is described comprising a microcontroller coupled to a transformer, wherein the transformer comprises a primary winding and a secondary winding, wherein the microcontroller is connected to a secondary circuit at a first location. The microcontroller is configured to provide a voltage at a first value to the primary winding for a period of time, wherein ceasing the delivery of the voltage induces a flow of current through the secondary winding and the secondary circuit, wherein the secondary circuit comprises at least one resistor and a resistive load, wherein the resistive load is variable. The microcontroller is configured to measure and/or compute voltage, time constant and peak current values with respect to the secondary circuit. The microcontroller is configured to monitor the intensity level at the resistive load using peak current and time constant values.

1 Claim, 11 Drawing Sheets

(56) References Cited

U.S. PATENT DOCUMENTS

| | | |
|---|---|---|
| 3,184,730 A | 5/1965 | Irish |
| 3,500,373 A | 3/1970 | Arthur |
| 3,735,757 A | 5/1973 | MacFarland |
| 4,180,013 A | 12/1979 | Smith |
| 4,426,884 A | 1/1984 | Polchaninoff |
| 4,783,646 A | 11/1988 | Matsuzaki |
| 4,794,402 A | 12/1988 | Gonda et al. |
| 4,802,482 A | 2/1989 | Gonda et al. |
| 4,947,795 A | 8/1990 | Farkas |
| 4,969,418 A | 11/1990 | Jones |
| 5,054,428 A | 10/1991 | Farkus |
| 5,159,580 A | 10/1992 | Andersen et al. |
| 5,161,485 A | 11/1992 | McDade |
| 5,182,032 A | 1/1993 | Dickie et al. |
| 5,207,178 A | 5/1993 | McDade et al. |
| 5,207,179 A | 5/1993 | Arthur et al. |
| 5,526,006 A | 6/1996 | Akahane et al. |
| 5,559,498 A | 9/1996 | Westrick et al. |
| 5,576,972 A | 11/1996 | Harrison |
| 5,586,521 A | 12/1996 | Kelley |
| 5,601,054 A | 2/1997 | So |
| 5,642,690 A | 7/1997 | Calabrese et al. |
| 5,794,569 A | 8/1998 | Titus et al. |
| 5,815,077 A | 9/1998 | Christiansen |
| 5,844,489 A | 12/1998 | Yarnall, Jr. et al. |
| 5,857,433 A | 1/1999 | Files |
| 5,870,029 A | 2/1999 | Otto et al. |
| 5,872,516 A | 2/1999 | Bonge, Jr. |
| 5,886,669 A | 3/1999 | Kita |
| 5,913,284 A | 6/1999 | Van Curen et al. |
| 5,923,254 A | 7/1999 | Brune |
| 5,927,233 A | 7/1999 | Mainini et al. |
| 5,933,079 A | 8/1999 | Frink |
| 5,934,225 A | 8/1999 | Williams |
| 5,949,350 A | 9/1999 | Girard et al. |
| 5,957,983 A | 9/1999 | Tominaga |
| 5,982,291 A | 11/1999 | Williams et al. |
| 6,016,100 A | 1/2000 | Boyd et al. |
| 6,019,066 A | 2/2000 | Taylor |
| 6,028,531 A | 2/2000 | Wanderlich |
| 6,047,664 A | 4/2000 | Lyerly |
| 6,067,018 A | 5/2000 | Skelton et al. |
| 6,075,443 A | 6/2000 | Schepps et al. |
| 6,166,643 A | 12/2000 | Janning et al. |
| 6,170,439 B1 | 1/2001 | Duncan et al. |
| 6,184,790 B1 | 2/2001 | Gerig |
| 6,196,990 B1 | 3/2001 | Zicherman |
| 6,204,762 B1 | 3/2001 | Dering et al. |
| 6,215,314 B1 | 4/2001 | Frankewich, Jr. |
| 6,230,031 B1 | 5/2001 | Barber |
| 6,230,661 B1 | 5/2001 | Yarnall, Jr. et al. |
| 6,232,880 B1 | 5/2001 | Anderson et al. |
| 6,271,757 B1 | 8/2001 | Touchton et al. |
| 6,327,999 B1 | 12/2001 | Gerig |
| 6,353,390 B1 | 3/2002 | Beri et al. |
| 6,360,697 B1 | 3/2002 | Williams |
| 6,360,698 B1 | 3/2002 | Stapelfeld et al. |
| 6,404,338 B1 | 6/2002 | Koslar |
| 6,415,742 B1 | 7/2002 | Lee et al. |
| 6,426,464 B1 | 7/2002 | Spellman et al. |
| 6,427,079 B1 | 7/2002 | Schneider et al. |
| 6,431,121 B1 | 8/2002 | Mainini et al. |
| 6,431,122 B1 | 8/2002 | Westrick et al. |
| 6,441,778 B1 | 8/2002 | Durst et al. |
| 6,459,378 B2 | 10/2002 | Gerig |
| 6,487,992 B1 | 12/2002 | Hollis |
| 6,561,137 B2 | 5/2003 | Oakman |
| 6,581,546 B1 | 6/2003 | Dalland et al. |
| 6,588,376 B1 | 7/2003 | Groh |
| 6,598,563 B2 | 7/2003 | Kim et al. |
| 6,600,422 B2 | 7/2003 | Barry et al. |
| 6,637,376 B2 | 10/2003 | Lee et al. |
| 6,657,544 B2 | 12/2003 | Barry et al. |
| 6,668,760 B2 | 12/2003 | Groh et al. |
| 6,700,492 B2 | 3/2004 | Touchton et al. |
| 6,747,555 B2 | 6/2004 | Fellenstein et al. |
| 6,798,887 B1 | 9/2004 | Andre |
| 6,799,537 B1 | 10/2004 | Liao |
| 6,807,720 B2 | 10/2004 | Brune et al. |
| 6,820,025 B2 | 11/2004 | Bachmann et al. |
| 6,825,768 B2 | 11/2004 | Stapelfeld et al. |
| 6,830,012 B1 | 12/2004 | Swan |
| 6,833,790 B2 | 12/2004 | Mejia et al. |
| 6,874,447 B1 | 4/2005 | Kobett |
| 6,888,502 B2 | 5/2005 | Beigel et al. |
| 6,901,883 B2 | 6/2005 | Gillis et al. |
| 6,903,682 B1 | 6/2005 | Maddox |
| 6,907,844 B1 | 6/2005 | Crist et al. |
| 6,907,883 B2 | 6/2005 | Lin |
| 6,921,089 B2 | 7/2005 | Groh et al. |
| 6,923,146 B2 | 8/2005 | Korbitz et al. |
| 6,928,958 B2 | 8/2005 | Crist et al. |
| 6,937,647 B1 | 8/2005 | Boyd et al. |
| 6,956,483 B2 | 10/2005 | Schmitt et al. |
| 6,970,090 B1 | 11/2005 | Sciarra |
| 7,061,385 B2 | 6/2006 | Fong et al. |
| 7,079,024 B2 | 7/2006 | Alarcon et al. |
| 7,114,466 B1 | 10/2006 | Mayer |
| 7,142,167 B2 | 11/2006 | Rochelle et al. |
| 7,164,354 B1 | 1/2007 | Panzer |
| 7,173,535 B2 | 2/2007 | Bach et al. |
| 7,198,009 B2 | 4/2007 | Crist et al. |
| 7,222,589 B2 | 5/2007 | Lee et al. |
| 7,249,572 B2 | 7/2007 | Goetzl et al. |
| 7,252,051 B2 | 8/2007 | Napolez et al. |
| 7,259,718 B2 | 8/2007 | Patterson et al. |
| 7,267,081 B2 | 9/2007 | Steinbacher |
| 7,275,502 B2 | 10/2007 | Boyd et al. |
| 7,296,540 B2 | 11/2007 | Boyd |
| 7,319,397 B2 | 1/2008 | Chung et al. |
| 7,328,671 B2 | 2/2008 | Kates |
| 7,339,474 B2 | 3/2008 | Easley et al. |
| 7,382,328 B2 | 6/2008 | Lee et al. |
| 7,394,390 B2 | 7/2008 | Gerig |
| 7,395,966 B2 | 7/2008 | Braiman |
| 7,404,379 B2 | 7/2008 | Nottingham et al. |
| 7,411,492 B2 | 8/2008 | Greenberg et al. |
| 7,426,906 B2 | 9/2008 | Nottingham et al. |
| 7,434,541 B2 | 10/2008 | Kates |
| 7,443,298 B2 | 10/2008 | Cole et al. |
| 7,477,155 B2 | 1/2009 | Bach et al. |
| 7,503,285 B2 | 3/2009 | Mainini et al. |
| 7,518,275 B2 | 4/2009 | Suzuki et al. |
| 7,518,522 B2 | 4/2009 | So et al. |
| 7,538,679 B2 | 5/2009 | Shanks |
| 7,546,817 B2 | 6/2009 | Moore |
| 7,552,699 B2 | 6/2009 | Moore |
| 7,562,640 B2 | 7/2009 | Lalor |
| 7,565,885 B2 | 7/2009 | Moore |
| 7,574,979 B2 | 8/2009 | Nottingham et al. |
| 7,583,931 B2 | 9/2009 | Eu et al. |
| 7,602,302 B2 | 10/2009 | Hokuf et al. |
| 7,612,668 B2 | 11/2009 | Harvey |
| 7,616,124 B2 | 11/2009 | Paessel et al. |
| 7,656,291 B2 | 2/2010 | Rochelle et al. |
| 7,667,599 B2 | 2/2010 | Mainini et al. |
| 7,667,607 B2 | 2/2010 | Gerig et al. |
| 7,680,645 B2 | 3/2010 | Li et al. |
| 7,705,736 B1 | 4/2010 | Kedziora |
| 7,710,263 B2 | 5/2010 | Boyd |
| 7,760,137 B2 | 7/2010 | Martucci et al. |
| 7,779,788 B2 | 8/2010 | Moore |
| 7,786,876 B2 | 8/2010 | Troxler et al. |
| 7,804,724 B2 | 9/2010 | Way |
| 7,814,865 B2 | 10/2010 | Tracy et al. |
| 7,828,221 B2 | 11/2010 | Kwon |
| 7,830,257 B2 | 11/2010 | Hassell |
| 7,834,769 B2 | 11/2010 | Hinkle et al. |
| 7,841,301 B2 | 11/2010 | Mainini et al. |
| 7,856,947 B2 | 12/2010 | Giunta |
| 7,864,057 B2 | 1/2011 | Milnes et al. |
| 7,868,912 B2 | 1/2011 | Venetianer et al. |
| 7,900,585 B2 | 3/2011 | Lee et al. |
| 7,918,190 B2 | 4/2011 | Belcher et al. |

(56) References Cited

U.S. PATENT DOCUMENTS

| | | |
|---|---|---|
| 7,944,359 B2 | 5/2011 | Fong et al. |
| 7,946,252 B2 | 5/2011 | Lee et al. |
| 7,978,078 B2 | 7/2011 | Copeland et al. |
| 7,996,983 B2 | 8/2011 | Lee et al. |
| 8,011,327 B2 | 9/2011 | Mainini et al. |
| 8,047,161 B2 | 11/2011 | Moore et al. |
| 8,049,630 B2 | 11/2011 | Chao et al. |
| 8,065,978 B2 | 11/2011 | Duncan et al. |
| 8,069,823 B2 | 12/2011 | Mainini et al. |
| 8,098,164 B2 | 1/2012 | Gerig et al. |
| 8,159,355 B2 | 4/2012 | Gerig et al. |
| 8,185,345 B2 | 5/2012 | Mainini |
| 8,232,909 B2 | 7/2012 | Kroeger et al. |
| 8,240,085 B2 | 8/2012 | Hill |
| 8,269,504 B2 | 9/2012 | Gerig |
| 8,274,396 B2 | 9/2012 | Gurley et al. |
| 8,297,233 B2 | 10/2012 | Rich et al. |
| 8,342,134 B2 | 1/2013 | Lee et al. |
| 8,342,135 B2 | 1/2013 | Peinetti et al. |
| 8,430,064 B2 | 4/2013 | Groh et al. |
| 8,436,735 B2 | 5/2013 | Mainini et al. |
| 8,447,510 B2 | 5/2013 | Fitzpatrick et al. |
| 8,451,130 B2 | 5/2013 | Mainini |
| 8,456,296 B2 | 6/2013 | Piltonen et al. |
| 8,483,262 B2 | 7/2013 | Mainini et al. |
| 8,714,113 B2 | 5/2014 | Lee et al. |
| 8,715,824 B2 | 5/2014 | Rawlings et al. |
| 8,736,499 B2 | 5/2014 | Goetzl et al. |
| 8,779,925 B2 | 7/2014 | Rich et al. |
| 8,803,692 B2 | 8/2014 | Goetzl et al. |
| 8,807,089 B2 | 8/2014 | Brown et al. |
| 8,823,513 B2 | 9/2014 | Jameson et al. |
| 8,854,215 B1 | 10/2014 | Ellis et al. |
| 8,866,605 B2 | 10/2014 | Gibson |
| 8,908,034 B2 | 12/2014 | Bordonaro |
| 8,917,172 B2 | 12/2014 | Charych |
| 8,947,240 B2 | 2/2015 | Mainini |
| 8,967,085 B2 | 3/2015 | Gillis et al. |
| 9,035,773 B2 | 5/2015 | Petersen et al. |
| 9,125,380 B2 | 9/2015 | Deutsch |
| 9,131,660 B2 | 9/2015 | Womble |
| 9,186,091 B2 | 11/2015 | Mainini et al. |
| 9,204,251 B1 | 12/2015 | Mendelson et al. |
| 9,307,745 B2 | 4/2016 | Mainini |
| 9,861,076 B2 | 1/2018 | Rochelle et al. |
| 1,051,443 A1 | 12/2019 | Seltzer |
| 2002/0010390 A1 | 1/2002 | Guice et al. |
| 2002/0015094 A1 | 2/2002 | Kuwano et al. |
| 2002/0036569 A1 | 3/2002 | Martin |
| 2002/0092481 A1 | 7/2002 | Spooner |
| 2002/0103610 A1 | 8/2002 | Bachmann et al. |
| 2002/0196151 A1 | 12/2002 | Troxler |
| 2003/0034887 A1 | 2/2003 | Crabtree et al. |
| 2003/0035051 A1 | 2/2003 | Cho et al. |
| 2003/0116099 A1 | 6/2003 | Kim et al. |
| 2003/0154928 A1 | 8/2003 | Lee et al. |
| 2003/0169207 A1 | 9/2003 | Beigel et al. |
| 2003/0179140 A1 | 9/2003 | Patterson et al. |
| 2003/0218539 A1 | 11/2003 | Hight |
| 2004/0108939 A1 | 6/2004 | Giunta |
| 2004/0162875 A1 | 8/2004 | Brown |
| 2005/0000469 A1 | 1/2005 | Giunta et al. |
| 2005/0007251 A1 | 1/2005 | Crabtree et al. |
| 2005/0020279 A1 | 1/2005 | Markhovsky et al. |
| 2005/0035865 A1 | 2/2005 | Brennan et al. |
| 2005/0059909 A1 | 3/2005 | Burgess |
| 2005/0066912 A1 | 3/2005 | Korbitz et al. |
| 2005/0081797 A1 | 4/2005 | Laitinen et al. |
| 2005/0139169 A1 | 6/2005 | So et al. |
| 2005/0145196 A1 | 7/2005 | Crist et al. |
| 2005/0145198 A1 | 7/2005 | Crist et al. |
| 2005/0145200 A1 | 7/2005 | Napolez et al. |
| 2005/0172912 A1 | 8/2005 | Crist et al. |
| 2005/0217606 A1 | 10/2005 | Lee et al. |
| 2005/0231353 A1 | 10/2005 | Dipoala et al. |
| 2005/0235924 A1 | 10/2005 | Lee et al. |
| 2005/0258715 A1 | 11/2005 | Schlabach et al. |
| 2005/0263106 A1 | 12/2005 | Steinbacher |
| 2005/0280546 A1 | 12/2005 | Ganley et al. |
| 2005/0288007 A1 | 12/2005 | Benco et al. |
| 2006/0000015 A1 | 1/2006 | Duncan |
| 2006/0011145 A1 | 1/2006 | Kates et al. |
| 2006/0027185 A1 | 2/2006 | Troxler et al. |
| 2006/0092676 A1 | 5/2006 | Liptak et al. |
| 2006/0102100 A1 | 5/2006 | Becker et al. |
| 2006/0102101 A1 | 5/2006 | Kim |
| 2006/0112901 A1 | 6/2006 | Gomez |
| 2006/0191491 A1 | 8/2006 | Nottingham et al. |
| 2006/0196445 A1 | 9/2006 | Kates |
| 2006/0197672 A1 | 9/2006 | Talamas, Jr. et al. |
| 2006/0202818 A1 | 9/2006 | Greenberg et al. |
| 2007/0011339 A1 | 1/2007 | Brown |
| 2007/0103296 A1 | 5/2007 | Paessel et al. |
| 2007/0197878 A1 | 8/2007 | Shklarski |
| 2007/0204803 A1 | 9/2007 | Ramsay |
| 2007/0204804 A1 | 9/2007 | Swanson et al. |
| 2007/0209604 A1 | 9/2007 | Groh et al. |
| 2007/0249470 A1 | 10/2007 | Niva et al. |
| 2007/0266959 A1 | 11/2007 | Brooks et al. |
| 2008/0004539 A1 | 1/2008 | Ross |
| 2008/0017133 A1 | 1/2008 | Moore |
| 2008/0036610 A1 | 2/2008 | Hokuf et al. |
| 2008/0055154 A1 | 3/2008 | Martucci et al. |
| 2008/0055155 A1 | 3/2008 | Hensley et al. |
| 2008/0058670 A1 | 3/2008 | Mainini et al. |
| 2008/0061978 A1 | 3/2008 | Huang |
| 2008/0061990 A1 | 3/2008 | Milnes et al. |
| 2008/0119757 A1 | 5/2008 | Winter |
| 2008/0129457 A1 | 6/2008 | Ritter et al. |
| 2008/0141949 A1 | 6/2008 | Taylor |
| 2008/0143516 A1 | 6/2008 | Mock et al. |
| 2008/0156277 A1 | 7/2008 | Mainini et al. |
| 2008/0163827 A1 | 7/2008 | Goetzl |
| 2008/0163829 A1 | 7/2008 | Lee et al. |
| 2008/0168949 A1 | 7/2008 | Belcher et al. |
| 2008/0168950 A1 | 7/2008 | Moore et al. |
| 2008/0186167 A1 | 8/2008 | Ramachandra |
| 2008/0186197 A1 | 8/2008 | Rochelle et al. |
| 2008/0204322 A1 | 8/2008 | Oswald et al. |
| 2008/0216766 A1 | 9/2008 | Martin et al. |
| 2008/0236514 A1 | 10/2008 | Johnson et al. |
| 2008/0252527 A1 | 10/2008 | Garcia |
| 2008/0272908 A1 | 11/2008 | Boyd |
| 2009/0000566 A1 | 1/2009 | Kim |
| 2009/0002188 A1 | 1/2009 | Greenberg |
| 2009/0012355 A1 | 1/2009 | Lin |
| 2009/0020002 A1 | 1/2009 | Williams et al. |
| 2009/0025651 A1 | 1/2009 | Lalor |
| 2009/0031966 A1 | 2/2009 | Kates |
| 2009/0061772 A1 | 3/2009 | Moon et al. |
| 2009/0082830 A1 | 3/2009 | Folkerts et al. |
| 2009/0102668 A1 | 4/2009 | Thompson et al. |
| 2009/0112284 A1* | 4/2009 | Smith .................. A61N 1/08 607/46 |
| 2009/0224909 A1 | 9/2009 | Derrick et al. |
| 2009/0239586 A1 | 9/2009 | Boeve et al. |
| 2009/0289785 A1 | 11/2009 | Leonard |
| 2009/0289844 A1 | 11/2009 | Palsgrove et al. |
| 2010/0008011 A1 | 1/2010 | Ogram |
| 2010/0033339 A1 | 2/2010 | Gurley et al. |
| 2010/0047119 A1 | 2/2010 | Cressy |
| 2010/0049364 A1 | 2/2010 | Landry et al. |
| 2010/0050954 A1 | 3/2010 | Lee, IV et al. |
| 2010/0107985 A1 | 5/2010 | O'Hare |
| 2010/0139576 A1 | 6/2010 | Kim et al. |
| 2010/0154721 A1 | 6/2010 | Gerig et al. |
| 2010/0231391 A1 | 9/2010 | Dror et al. |
| 2010/0238022 A1 | 9/2010 | Au et al. |
| 2010/0315241 A1 | 12/2010 | Jow |
| 2011/0140967 A1 | 6/2011 | Lopez et al. |
| 2012/0000431 A1 | 1/2012 | Khoshkish et al. |
| 2012/0006282 A1 | 1/2012 | Kates |
| 2012/0037088 A1 | 2/2012 | Altenhofen |
| 2012/0078139 A1 | 3/2012 | Aldridge et al. |

(56) References Cited

U.S. PATENT DOCUMENTS

| | | |
|---|---|---|
| 2012/0132151 A1 | 5/2012 | Touchton et al. |
| 2012/0165012 A1 | 6/2012 | Fischer et al. |
| 2012/0188370 A1 | 7/2012 | Bordonaro |
| 2012/0236688 A1 | 9/2012 | Spencer et al. |
| 2012/0312250 A1 | 12/2012 | Jesurum |
| 2013/0099920 A1 | 4/2013 | Song et al. |
| 2013/0099922 A1 | 4/2013 | Lohbihler |
| 2013/0141237 A1 | 6/2013 | Goetzl et al. |
| 2013/0157564 A1 | 6/2013 | Curtis et al. |
| 2013/0169441 A1 | 7/2013 | Wilson |
| 2013/0298846 A1 | 11/2013 | Mainini |
| 2013/0321159 A1 | 12/2013 | Schofield et al. |
| 2014/0020635 A1 | 1/2014 | Sayers et al. |
| 2014/0053788 A1 | 2/2014 | Riddell |
| 2014/0062695 A1 | 3/2014 | Rosen et al. |
| 2014/0069350 A1 | 3/2014 | Riddell |
| 2014/0073939 A1 | 3/2014 | Rodriguez-Llorente et al. |
| 2014/0120943 A1 | 5/2014 | Shima |
| 2014/0123912 A1 | 5/2014 | Menkes et al. |
| 2014/0132608 A1 | 5/2014 | Mund et al. |
| 2014/0174376 A1 | 6/2014 | Touchton et al. |
| 2014/0228649 A1 | 8/2014 | Rayner et al. |
| 2014/0228927 A1* | 8/2014 | Ahmad ............... A61N 1/36014 607/148 |
| 2014/0253389 A1 | 9/2014 | Beauregard |
| 2014/0261235 A1 | 9/2014 | Rich et al. |
| 2014/0267299 A1 | 9/2014 | Couse |
| 2014/0275824 A1 | 9/2014 | Couse et al. |
| 2014/0276278 A1 | 9/2014 | Smith et al. |
| 2014/0307888 A1 | 10/2014 | Alderson et al. |
| 2014/0320347 A1 | 10/2014 | Rochelle et al. |
| 2014/0343599 A1 | 11/2014 | Smith et al. |
| 2015/0040840 A1 | 2/2015 | Muetzel et al. |
| 2015/0043744 A1 | 2/2015 | Lagodzinski et al. |
| 2015/0053144 A1 | 2/2015 | Bianchi et al. |
| 2015/0075446 A1 | 3/2015 | Hu |
| 2015/0080013 A1 | 3/2015 | Venkatraman et al. |
| 2015/0107531 A1 | 4/2015 | Golden |
| 2015/0149111 A1 | 5/2015 | Kelly et al. |
| 2015/0163412 A1 | 6/2015 | Holley et al. |
| 2015/0172872 A1 | 6/2015 | Alsehly |
| 2015/0173327 A1 | 6/2015 | Gerig et al. |
| 2015/0199490 A1 | 7/2015 | Iancu et al. |
| 2015/0223013 A1 | 8/2015 | Park et al. |
| 2015/0289111 A1 | 10/2015 | Ozkan et al. |
| 2015/0350848 A1 | 12/2015 | Eramian |
| 2015/0358768 A1 | 12/2015 | Luna et al. |
| 2016/0015005 A1 | 1/2016 | Brown, Jr. et al. |
| 2016/0021506 A1 | 1/2016 | Bonge, Jr. |
| 2016/0021850 A1 | 1/2016 | Stapelfeld et al. |
| 2016/0029466 A1 | 1/2016 | Demao et al. |
| 2016/0044444 A1 | 2/2016 | Rattner et al. |
| 2016/0084801 A1 | 3/2016 | Robinson et al. |
| 2016/0094419 A1 | 3/2016 | Peacock et al. |
| 2016/0102879 A1 | 4/2016 | Guest et al. |
| 2016/0150362 A1 | 5/2016 | Shaprio et al. |
| 2016/0174099 A1 | 6/2016 | Goldfain |
| 2016/0178392 A1 | 6/2016 | Goldfain |
| 2016/0187454 A1 | 6/2016 | Orman et al. |
| 2016/0253987 A1 | 9/2016 | Chattell |
| 2016/0335917 A1 | 11/2016 | Lydecker et al. |
| 2016/0363664 A1 | 12/2016 | Mindell et al. |
| 2017/0323630 A1 | 11/2017 | Stickney et al. |
| 2018/0027772 A1 | 2/2018 | Gordon et al. |
| 2018/0077509 A1 | 3/2018 | Jones et al. |
| 2018/0078735 A1 | 3/2018 | Dalgleish et al. |
| 2018/0094451 A1 | 4/2018 | Peter et al. |
| 2018/0188351 A1 | 7/2018 | Jones et al. |
| 2018/0210704 A1 | 7/2018 | Jones et al. |
| 2018/0234134 A1 | 8/2018 | Tang et al. |
| 2018/0235182 A1 | 8/2018 | Bocknek |
| 2018/0315262 A1 | 11/2018 | Love et al. |
| 2019/0013003 A1 | 1/2019 | Baughman et al. |
| 2019/0110430 A1 | 4/2019 | Badiou |
| 2019/0165832 A1 | 5/2019 | Khanduri et al. |

FOREIGN PATENT DOCUMENTS

| | | |
|---|---|---|
| CN | 101112181 B | 11/2012 |
| CN | 102793568 B | 12/2014 |
| JP | H0974774 A | 3/1997 |
| KR | 20130128704 A | 11/2013 |
| WO | WO-02060240 A3 | 2/2003 |
| WO | WO-2006000015 A1 | 1/2006 |
| WO | WO-2008085812 A2 | 7/2008 |
| WO | WO-2008140992 A1 | 11/2008 |
| WO | WO-2009105243 A2 | 8/2009 |
| WO | WO-2009106896 A2 | 9/2009 |
| WO | WO-2011055004 A1 | 5/2011 |
| WO | WO-2011136816 A1 | 11/2011 |
| WO | WO-2012122607 A1 | 9/2012 |
| WO | WO-2015015047 A1 | 2/2015 |
| WO | WO-2016204799 A1 | 12/2016 |

OTHER PUBLICATIONS

Baba A.I., et al., "Calibrating Time of Flight in Two Way Ranging," IEEE Xplore Digital Library, Dec. 2011, pp. 393-397.

Extended European Search Report for European Application No. 11784149.4 dated Nov. 17, 2017, 7 pages.

Extended European Search Report for European Application No. 15735439.0 dated Oct. 18, 2017, 9 pages.

Extended European Search Report for European Application No. 15895839.7 dated Oct. 9, 2018, 5 pages.

Extended European Search Report for European Application No. 17162289.7 dated Aug. 31, 2017, 7 pages.

High Tech Products, Inc: "Human Contain Model X-10 Rechargeable Muti-function Electronic Dog Fence Ultra-system", Internet citation, Retrieved from the Internet: URL:http://web.archive.org/web/20120112221915/http://hightechpet.com/user_Manuals/HC%20X-10_Press.pdf retrieved on Apr. 10, 2017], Apr. 28, 2012, pp. 1-32, XP008184171.

International Preliminary Report for Patentability Chapter II for International Application No. PCT/US2014/024875 dated Mar. 12, 2015, 17 pages.

International Preliminary Report on Patentability for Application No. PCT/US2015/043653 dated Dec. 19, 2017, 14 pages.

International Search Report and Written Opinion for Application No. PCT/US2018/013737 dated Mar. 7, 2018, 8 pages.

International Search Report and Written Opinion for Application No. PCT/US2018/013738 dated Mar. 20, 2018, 6 pages.

International Search Report and Written Opinion for Application No. PCT/US2018/013740 dated Mar. 20, 2018, 6 pages.

International Search Report and Written Opinion for Application No. PCT/US2018/019887 dated May 8, 2018, 10 pages.

International Search Report and Written Opinion for International Application No. PCT/US2014/024875 dated Jun. 27, 2014, 12 pages.

International Search Report for International Application No. PCT/US2014/020344 dated Jun. 5, 2014, 2 pages.

International Search Report for International Application No. PCT/US2014/066650 dated Feb. 19, 2015, 3 pages (Outgoing).

International Search Report for International Application No. PCT/US2015/010864, Form PCT/ISA/210 dated Apr. 13, 2015, 2 pages.

International Search Report for International Application No. PCT/US2015/043653, Form PCT/ISA/210 dated Oct. 23, 2015, 2 pages.

Notification of Transmittal of the International Search Report and the Written Opinion of the International Searching Authority for International Application No. PCT/US2015/043653, Form PCT/ISA/220 dated Oct. 23, 2015, 1 page.

Notification of Transmittal of the International Search Report and Written Opinion for the International Application No. PCT/US2014/066650 dated Feb. 19, 2015, 1 page.

Extended European Search Report for Application No. EP17180645, dated May 9, 2018, 5 pages.

Welch et al., "An Introduction to the Kalman Filter," Department of Computer Science, Jul. 24, 2006, pp. 1-16.

Written Opinion for International Application No. PCT/US2014/066650 dated Feb. 19, 2015, 15 pages(outgoing).

(56) References Cited

OTHER PUBLICATIONS

Written Opinion for International Application No. PCT/US2015/043653, Form PCT/ISA/237 dated Oct. 23, 2015, 13 pages.
Written Opinion of the International Application No. PCT/US2015/010864, Form PCT/ISA/237 dated Apr. 13, 2015, 6 pages.

* cited by examiner

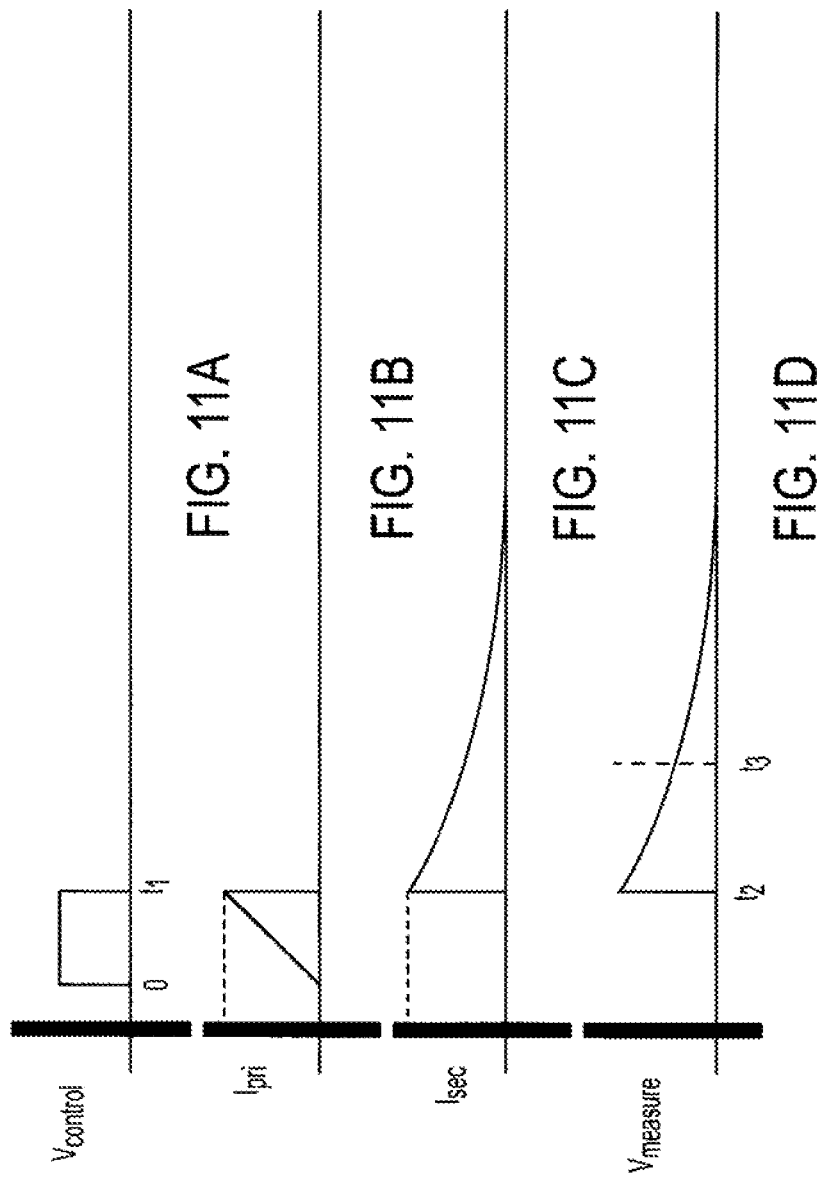

METHOD AND APPARATUS FOR APPLYING, MONITORING, AND ADJUSTING A STIMULUS TO A PET

RELATED APPLICATIONS

Not applicable

TECHNICAL FIELD

The disclosure herein involves dynamic voltage modulation.

BACKGROUND

Pet training and containment is essential for pet owners. One of the most common humane and effective training methods is electrical stimulation of the pet animal. Short electrical pulses are used to communicate desired behaviors. Currently, there is very little variance in stimulation delivery methods. Most typical methods deliver an electrical current directly from the output of a transformer with an assumption that energy is delivered successfully.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIG. 11A shows a one shot timer with interrupt for desired pulse width, under an embodiment.

FIG. 11B shows primary current as a function of time, under an embodiment.

FIG. 11C shows secondary current as a function of time, under an embodiment.

FIG. 11D shows sampled voltage measurements, under an embodiment.

DETAILED DESCRIPTION

Figure 1:
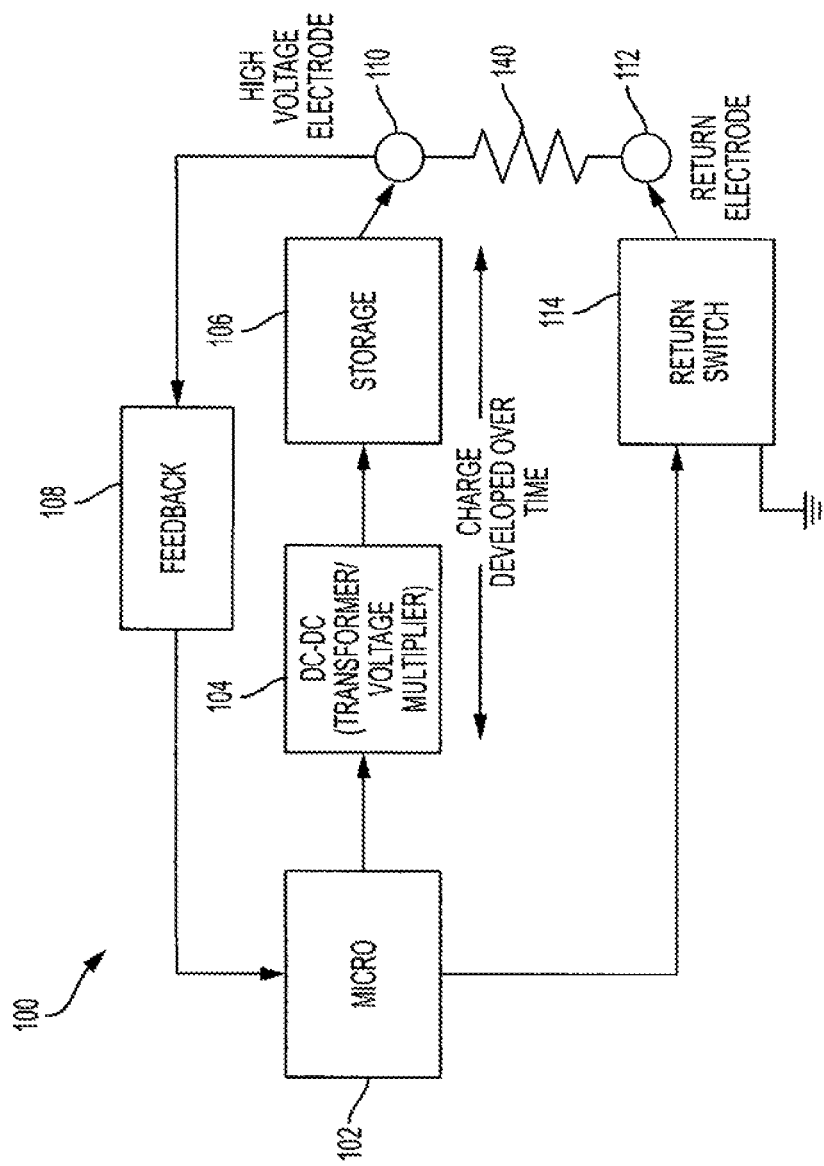
FIG. 1 shows a circuit for developing, applying, and monitoring stimulus levels in controlling delivery of electrical stimulation to an animal, under an embodiment.

Systems and methods for delivering electrical stimulation to an animal suffer an inability to deliver precise and accurate voltage levels, an inability to precisely adjust these levels, and lack of methods to reliably determine whether a charge is effectively delivered to the pet. This problem leads to under- or over-correction of the pet which may the lead to increased stress levels during the training process and therefore decreased effectiveness.

Systems and methods are herein proposed in this application that precisely deliver electrical pulses to the pet through electrodes and that are able to determine delivery effectiveness of these pulses in a measureable manner. Based on the measured delivery effectiveness of pulses, subsequent pulses may be adjusted to increase the chances of delivery effectiveness if it is determined that successful delivery has not yet occurred. Subsequent pulses may be adjusted to minimize pulse magnitudes to decrease stress to the pet while still maintaining effectiveness if it is determined that successful delivery has occurred.

The systems and methods proposed herein implement two capabilities:

An electrical stimulus pulse development of an embodiment uses a method to precisely control the voltage and timing of energy pulses that are delivered to the pet.

Load resistance may be accurately determined under an embodiment. Load resistance is an indicator of skin conduction, which is an indicator of pulse delivery effectiveness. Identifying the point in time when skin breakdown occurs allows for a reduction in voltage level on subsequent pulses while still eliciting a similar response. Identifying the fact that the skin is not breaking down due to stimulus pulses indicates a need to increase the voltage to maximize the chance of breakdown and conduction.

In addition to the voltage adjustment and effectiveness monitoring, the use of this new technology allows for a much smaller design. As the transformer is used in step-up mode to incrementally build up a charge within storage components until such time as a return path switch is activated, the size can be much smaller than with typical techniques as it is not required to deliver a charge from a single cycle of its magnetic potential. It may take several hundred, or even several thousand cycles of charge from the transformer to build up energy in the storage components before the energy is released. The fact that the system requires an extended period of time to restore the depleted energy means there is time to monitor and control the precise voltage and also determine effectiveness of the prior pulse due to the amount of energy required to refill the storage components.

The systems and methods described herein include a method used to develop, apply (release), analyze, and adjust electrical stimulus pulses based on the load conditions of the pet skin. The electrical stimulus approach utilizes a microprocessor to control all aspects of stimulus development, release, and monitoring. The microprocessor controls a switched mode power supply, consisting of transformer and voltage doubler(s) to step-up the input voltage. The voltage is presented to storage component(s) (typically capacitors) for storage which is exposed on an electrode. This stored charge is monitored by the processor via a feedback loop. Once the processor determines a threshold voltage level is reached and any additional desired delay time is added, a high voltage switch (i.e., transistor) is switched on by the processor for the desired stimulus pulse length to complete a return path on a second electrode providing a path for current to flow from one electrode, through the pet's skin, into the second electrode, and to system return.

It is also plausible that a switch be utilized on the high voltage side of the circuit to provide a path from the storage component to the electrode (high-side switch).

The feedback loop allows for real time monitoring of voltage level and charge time. This knowledge allows a processing unit to: (i) precisely and accurately determine the stimulus pulse magnitude and (ii) monitor the recharge time. The feedback loop therefore allows determination of the depleted charge using recharge time as a direct indicator of load resistance (skin resistance). Based on depleted charge findings, subsequent pulses may be:

increased to compensate for non-optimal dermal contact;
reduced to decrease stress on the pet, while maintaining training effectiveness; and/or
reduced to save energy as lower voltage pulses require less energy to be depleted from the system power supply.

FIG. 1 shows a circuit 100 for monitoring stimulus levels in controlling delivery of precise electrical stimulation to an animal. FIG. 1 shows a microcontroller 102 which controls a DC-DC converter (i.e. transformer plus voltage multiplier) 104 which steps up the input voltage. The stepped-up voltage is then presented to a storage component (typically capacitor(s)) 106 for storage. The storage component may include one or more capacitors which are connected to a first (high voltage) electrode 110. The circuit shown in FIG. 1 shows a feedback connection 108 between the first electrode and the microcontroller 102 such that the microcontroller may monitor potential energy at the first electrode. The microcontroller also controls a return switch 114. The microcontroller may then use the return switch 114 to provide a return path to voltage stored in the storage component after passing through the pet skin. The switch may comprise a transistor and may provide the return path for the desired stimulus pulse length. Stimulus delivery then comprises current flow from the first electrode 110 through the pet's skin (i.e. resistive load 140), into the second return electrode 112, and to system return (ground).

Figure 2:
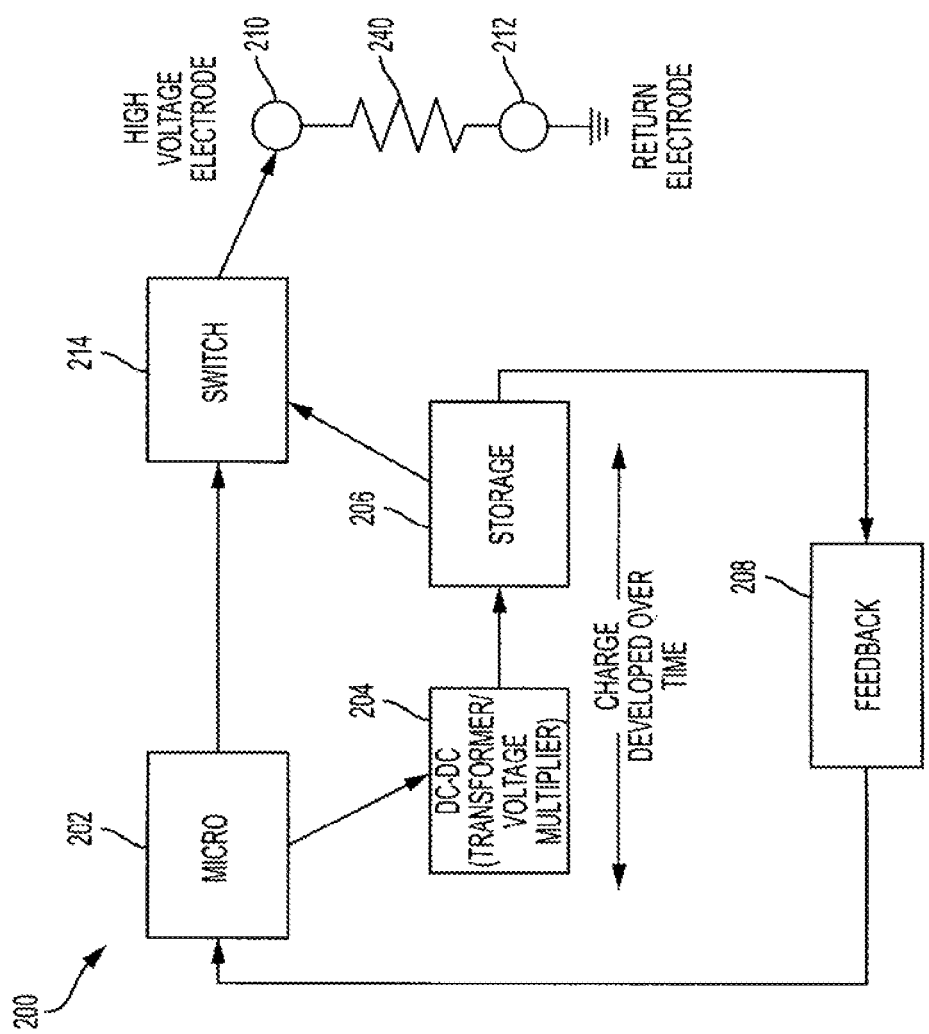
FIG. 2 shows a circuit for developing, applying, and monitoring stimulus levels in controlling delivery of electrical stimulation to an animal, under an embodiment.

FIG. 2 shows the same components of the circuit described above. However, the circuit 200 of FIG. 2 places the transistor switch 214 directly between the microcontroller 202 and the first electrode 210. The DC-DC converter 204 steps up voltage delivered by the microcontroller and charges the storage 206 component. A feedback connection 208 is provided between the storage component 206 and the microcontroller 202. The microcontroller 202 controls a transistor 214 in providing a pathway between the storage component 206 (charged by the DC-DC converter 204) and the first electrode 210 for a desired stimulus pulse length. During stimulus delivery, current flows from the storage component to the first electrode 210 through the pet's skin (or resistive load 240), into the second return electrode 212, and to system return (ground). In contrast to the circuit of FIG. 1, the return electrode 212, in contact with the animal skin, is always connected to system return (ground).

Figure 3:
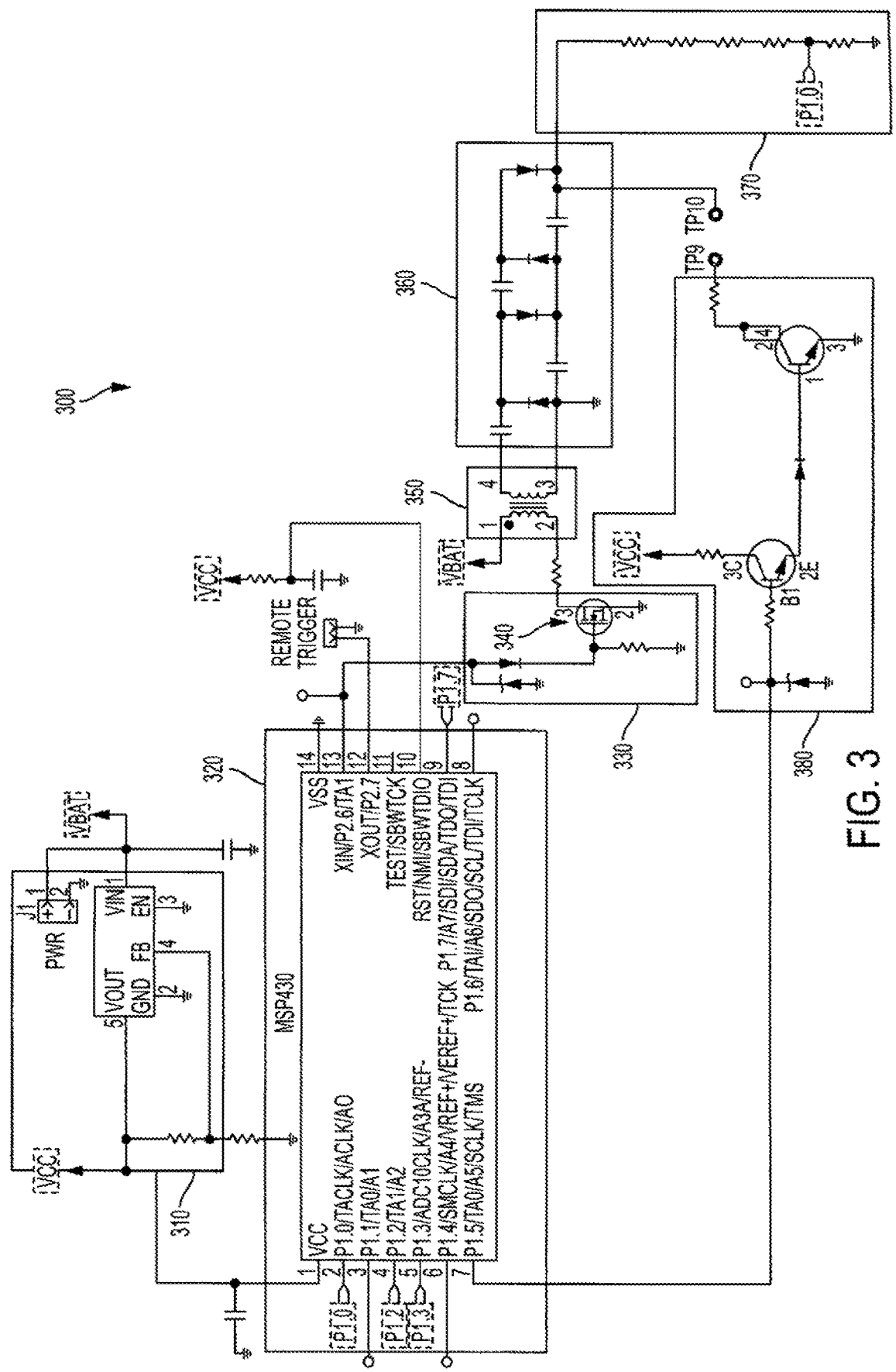
FIG. 3 shows a circuit for developing, applying, and monitoring stimulus levels in controlling delivery of electrical stimulation to an animal, under an embodiment.

FIG. 3 shows a circuit 300 for developing, applying and monitoring stimulus levels in controlling delivery of electrical stimulation to an animal, under an embodiment. FIG. 3 shows voltage regulator 310 and microprocessor 320. FIG. 3 shows the transformer-primary control 330. The Field-Effect Transistor (FET) 340 acts as a switch at a frequency and duty cycle to efficiently allow current to flow through the primary of the step-up transformer 350. Element 360 of FIG. 3 demonstrates two stages of voltage doublers, which creates a voltage quadrupler, under an embodiment. As many stages as required may be cascaded for the specific application (in combination with the turns ratio of the step-up transformer). Accordingly, the step-up transformer 350 and voltage quadrupler 360 component comprise a DC-DC Step-up converter. Voltage divider 370 reduces the high voltage output to a level compatible with the microprocessor inputs. FIG. 3 shows a controllable high voltage return path 380. This return path controls the duration of the stimulation pulse by providing a path from the high voltage electrode, through the skin, into the low side electrode, and to system ground.

Figure 4:
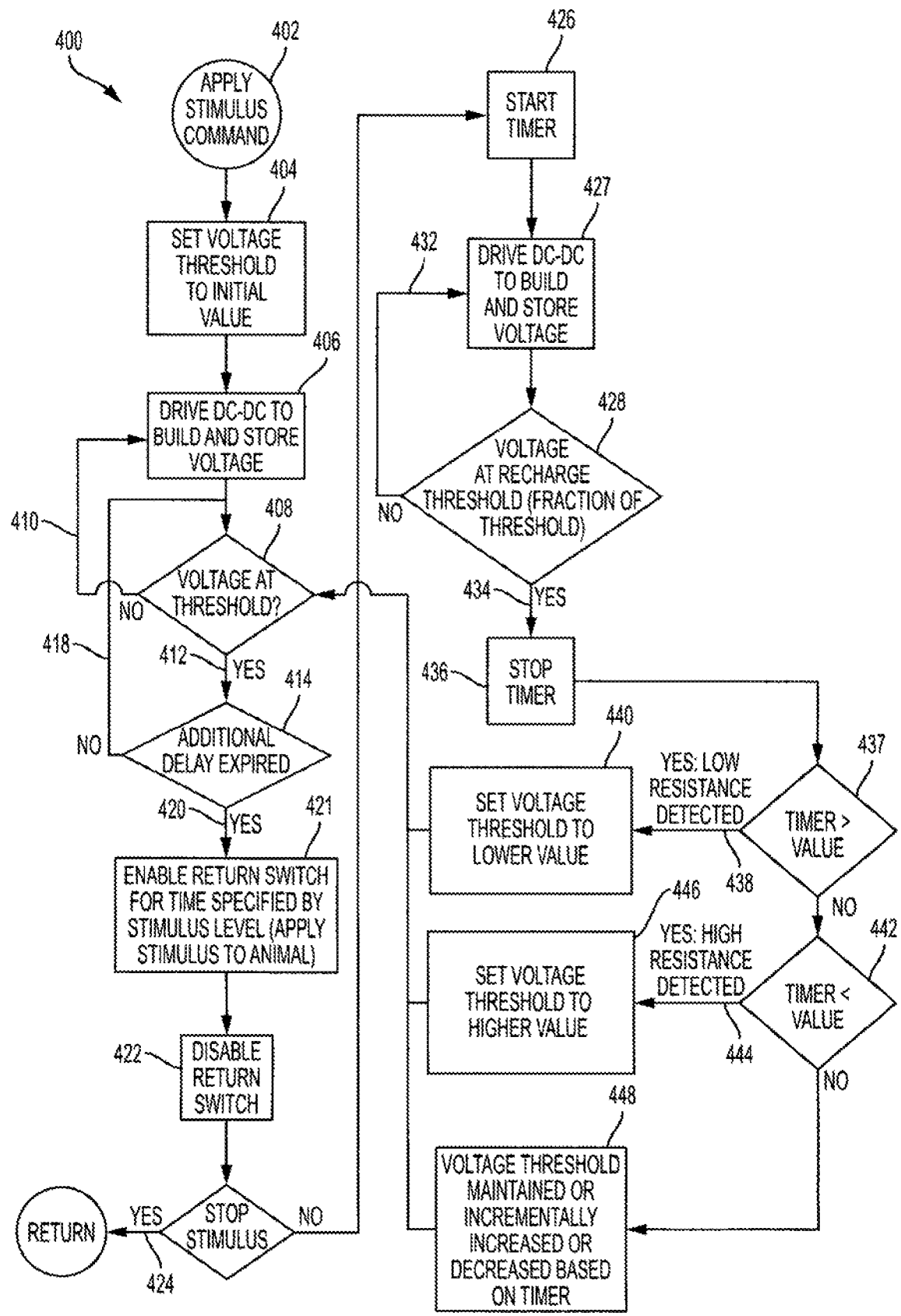
FIG. 4 shows a method for modulating delivery of electrical stimulus to an animal, under an embodiment.

FIG. 4 shows a method for modulating stimulus delivery to an animal. A first step 402 involves applying a stimulus command, i.e. a command to deliver an electrical stimulus using the feedback control circuit described herein. Step 404 comprises setting a voltage threshold to an initial value. Step 406 involves a microcontroller controlling a DC-DC converter to provide a voltage to a storage component to drive and build voltage potential. The method iteratively checks the voltage 408 to determine if a threshold is met. If no 410 then voltage development and storage continues. If yes 412, the method proceeds to step 414 to determine if an additional delay is expired. If not 418 then the method maintains voltage at the stored potential level. If the answer is yes 420 then the microcontroller enables the return switch for a time specified or determined by a given stimulus level 421, i.e. the stimulus is applied to the animal. The microcontroller then disables the switch 422, i.e. return pathway. If application of the stimulus command is discontinued 424, then the method of stimulus delivery is also discontinued.

If application of the stimulus command continues, the method starts a timer 426. As timer 426 runs, the microcontroller controls a DC-DC converter to provide a voltage to a storage component to drive and build voltage potential 427. Step 428 determines whether the stored voltage achieves a set threshold (which may be a fraction of the originally established threshold at step 408). If not 432, charging continues. Once this threshold voltage is realized 434, the method stops the timer 436. Measured time values provide information of skin breakdown. If the measured time value is greater than a value indicating breakdown 437, then low resistance is detected 438. In this event, the voltage threshold is set to a lower value considering that skin resistance is low 440. If the measured time value is less than a value indicating minimal to no skin contact 442, then high resistance is detected 444. In this event, the voltage threshold is set to a higher value to increase the chance of a low skin resistance scenario 446. If the method passes through steps 437 and 442 as a "no" then the method at step 448 may either maintain or incrementally increase the voltage threshold based on the timer value, under an embodiment. The method at step 448 may also incrementally decrease the voltage threshold based on the timer value, under an embodiment. After any of the three voltage threshold assessment events, the method returns to step 408 of the stimulus command workflow process.

Figure 5:
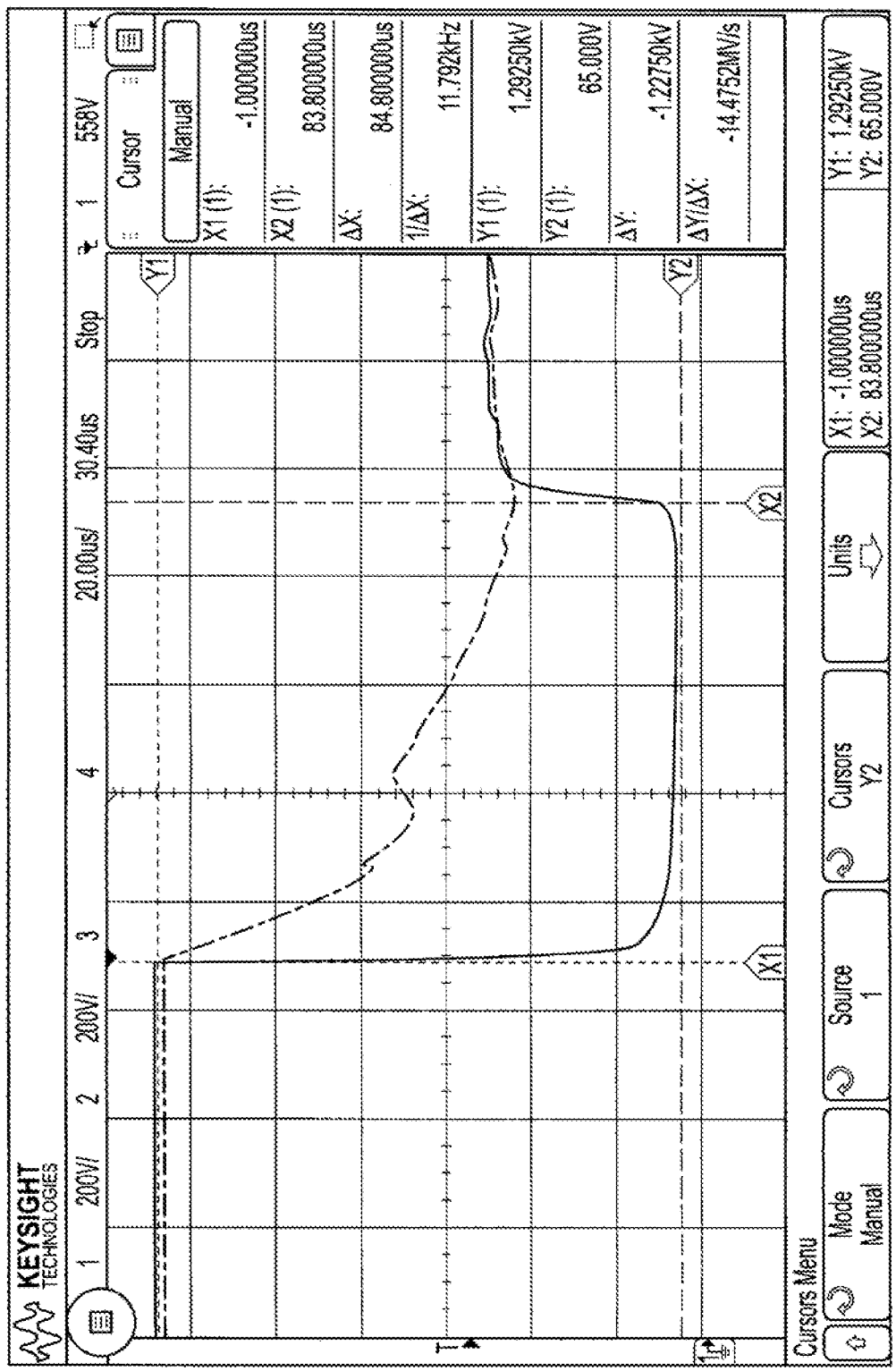
FIG. 5 shows an oscilloscope trace of a high voltage electrode and a return electrode, under an embodiment.

The oscilloscope trace of FIG. 5 shows the high voltage electrode and return electrode during the period where the return path switch is activated. In this example, this switch is activated for a period of time about 85 microseconds. The ground electrode attains a voltage equivalent to ground almost immediately. The high voltage electrode starts at the full storage component voltage level and decreases as energy is depleted.

This voltage drop is an indicator of the energy drawn from the system's storage. The lower the pet skin resistance, the more energy is being depleted from the system. The lower the pet skin resistance, the more energy that is being delivered to the pet.

During the single electrical pulse described (and illustrated) above, energy is drawn from the system storage. During this fixed period of time, the following equations can be applied to determine pet skin resistance, which is a direct indicator of effective pulse delivery:

E=energy in joules depleted from the storage component(s) during the stimulus pulse
P=power in watts at an instant of time
V=voltage differential across the electrodes
I=current flowing from the first electrode, through the animal, into the second electrode, to system ground.
R=resistance of the animal's skin
T=time in seconds that the pulse is applied to the animal's skin
---------

$P=VI=V^2/R$: Power at an instant of time
$E=PT=(V^2/R)*T$: Energy over a period of time (more specifically, during the stimulus pulse)
$R=(V^2T)/E$: Resistance of the animal's skin As can be seen from the preceding equations, energy and resistance have an inverse relationship. The higher the energy level depleted from the system (as determined by monitoring replenishment), the lower the resistance (of the pet's skin).

Long replenishment=more energy depleted=lower skin resistance
Shorter replenishment=less energy depleted=higher skin resistance Following application of the single pulse above, the system replenishes the system energy as is indicated in the following diagrams (depending on skin resistance).

The following oscilloscope traces seen in FIGS. 6-9 show the high voltage electrode and return electrode before stimulus delivery, during stimulus delivery, and when restoring the energy depleted during the stimulus delivery.

The start of the gap in the traces (seen in FIGS. 6-9) indicates the instant a short (i.e., 1 microsecond to 200 microsecond) pulse is activated by turning on the "return switch" to enable a return path from the return electrode to ground. This period is where current is allowed to flow from the high voltage electrode, through the skin of the pet, and then to system return (ground). Following this brief period, the remainder of the gap is the period of time required to recharge the storage component(s). This period of time indicates the energy drawn from the system's storage.

Figure 6:
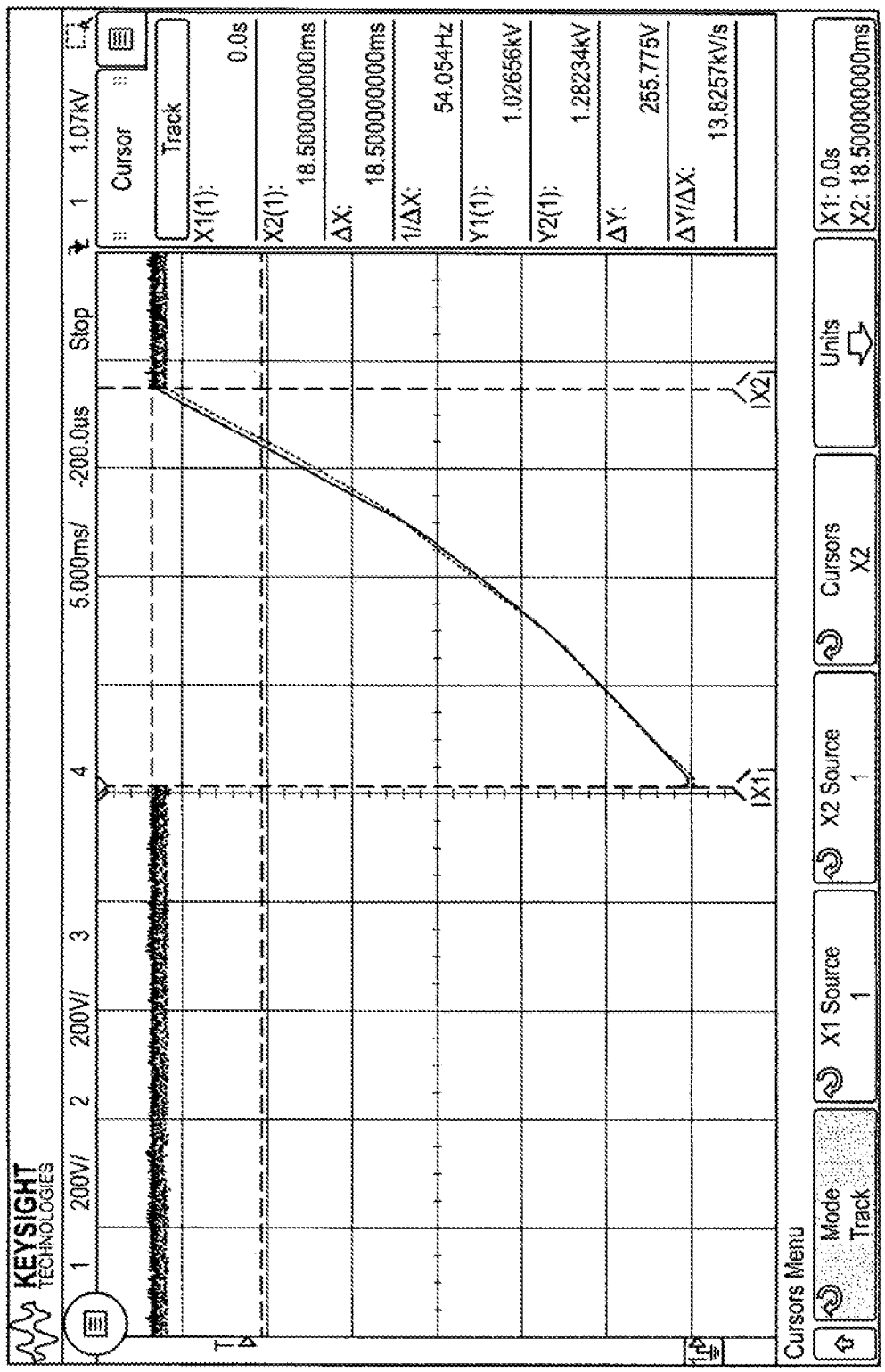
FIG. 6 shows a single electrical pulse followed by energy recovery, under an embodiment.

FIG. 6 shows a single electrical pulse followed by energy recovery assuming a 500 ohm skin resistance. A 500 ohm load indicates strong dermal contact. FIG. 6 shows an 18.5 ms recovery time (X1 to X2).

Figure 7:
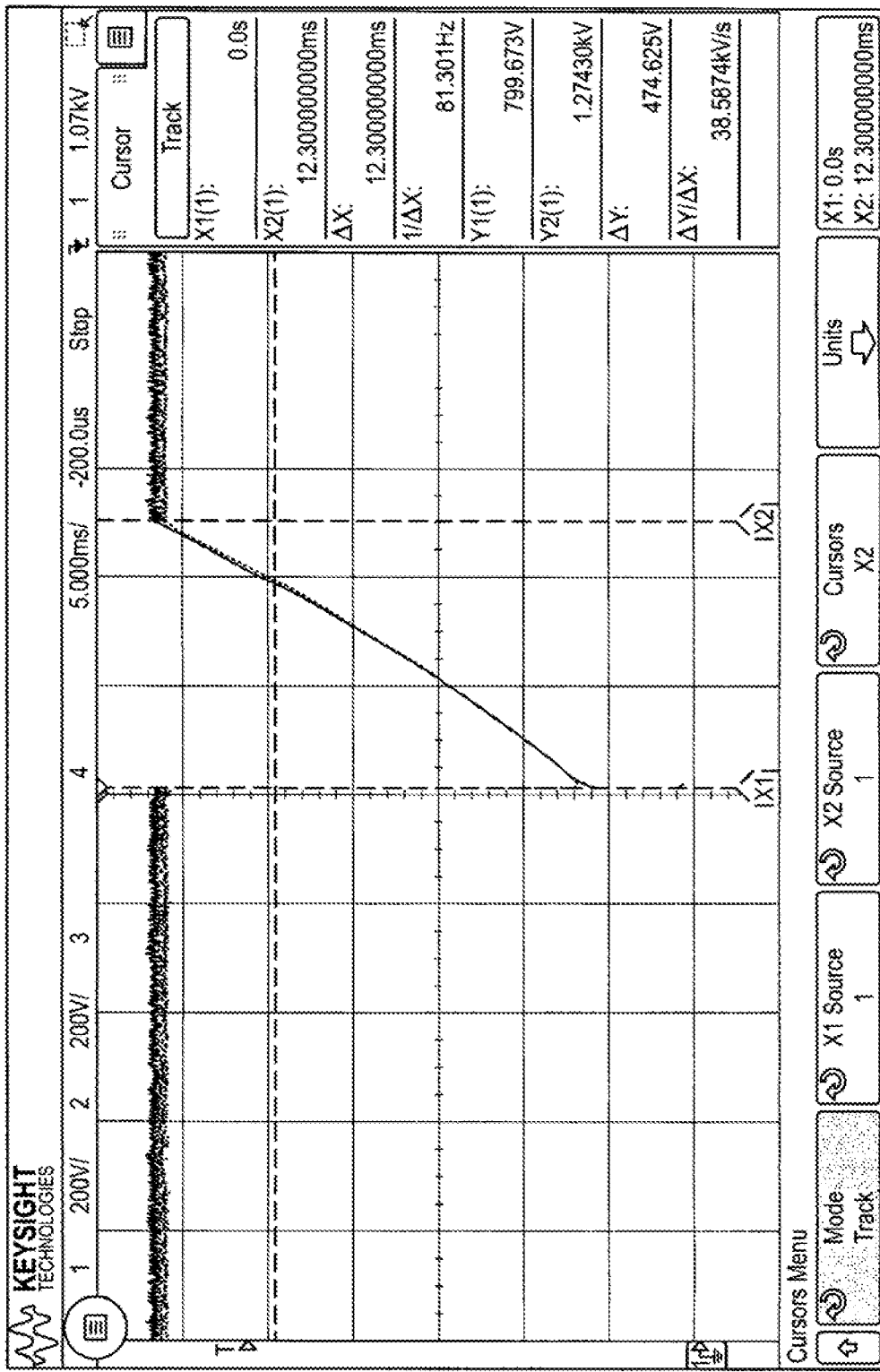
FIG. 7 shows a single electrical pulse followed by energy recovery, under an embodiment.

FIG. 7 shows a single electrical pulse followed by energy recovery assuming a 10K ohm skin resistance. A 10K ohm load indicates weak dermal contact. FIG. 7 shows a 12.3 ms recovery (X1 to X2).

Figure 8:
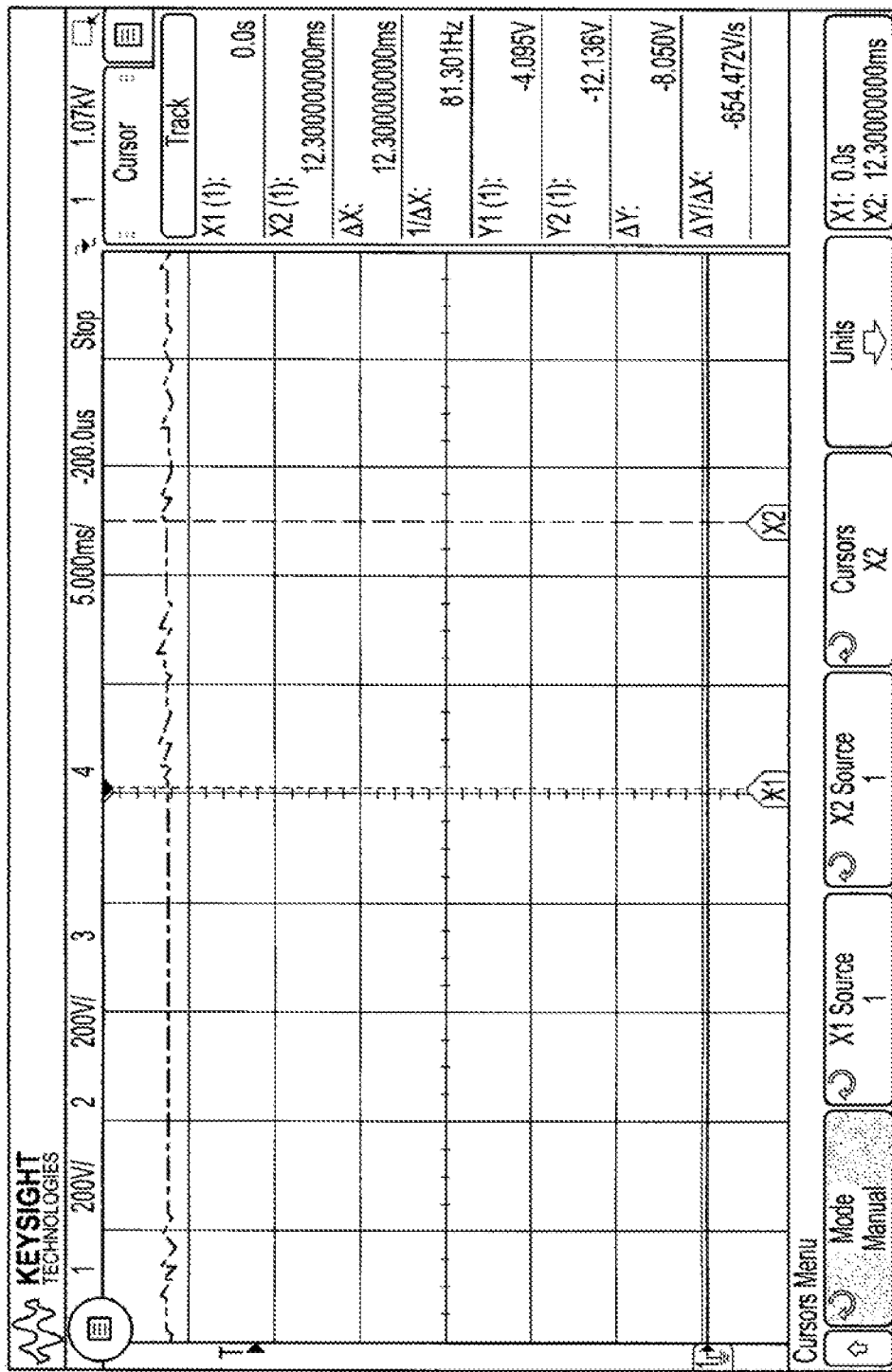
FIG. 8 shows a single electrical pulse followed by energy recovery, under an embodiment.

FIG. 8 shows a single electrical pulse followed by energy recovery assuming minimal to no skin resistance, i.e. weak dermal contact. The very high resistive load indicates minimal to no dermal contact. FIG. 8 shows an immediate recovery, indicating no energy was drained from the system during the stimulation.

If strong dermal contact is detected, subsequent pulses can be reduced in magnitude while still maintaining sufficient energy transfer. Again note that:

$R=(V^2T)/E$ $E=(V^2*T)/R$

Increased energy depletion indicates that skin resistance has decreased. Therefore, voltage can be decreased while still applying a sufficient stimulus.

If R (skin resistance) decreases due to skin breakdown following a high voltage pulse, voltage (V) can be reduced to transfer equivalent energy to the initial voltage applied as can be seen in the above equations.

Figure 9:
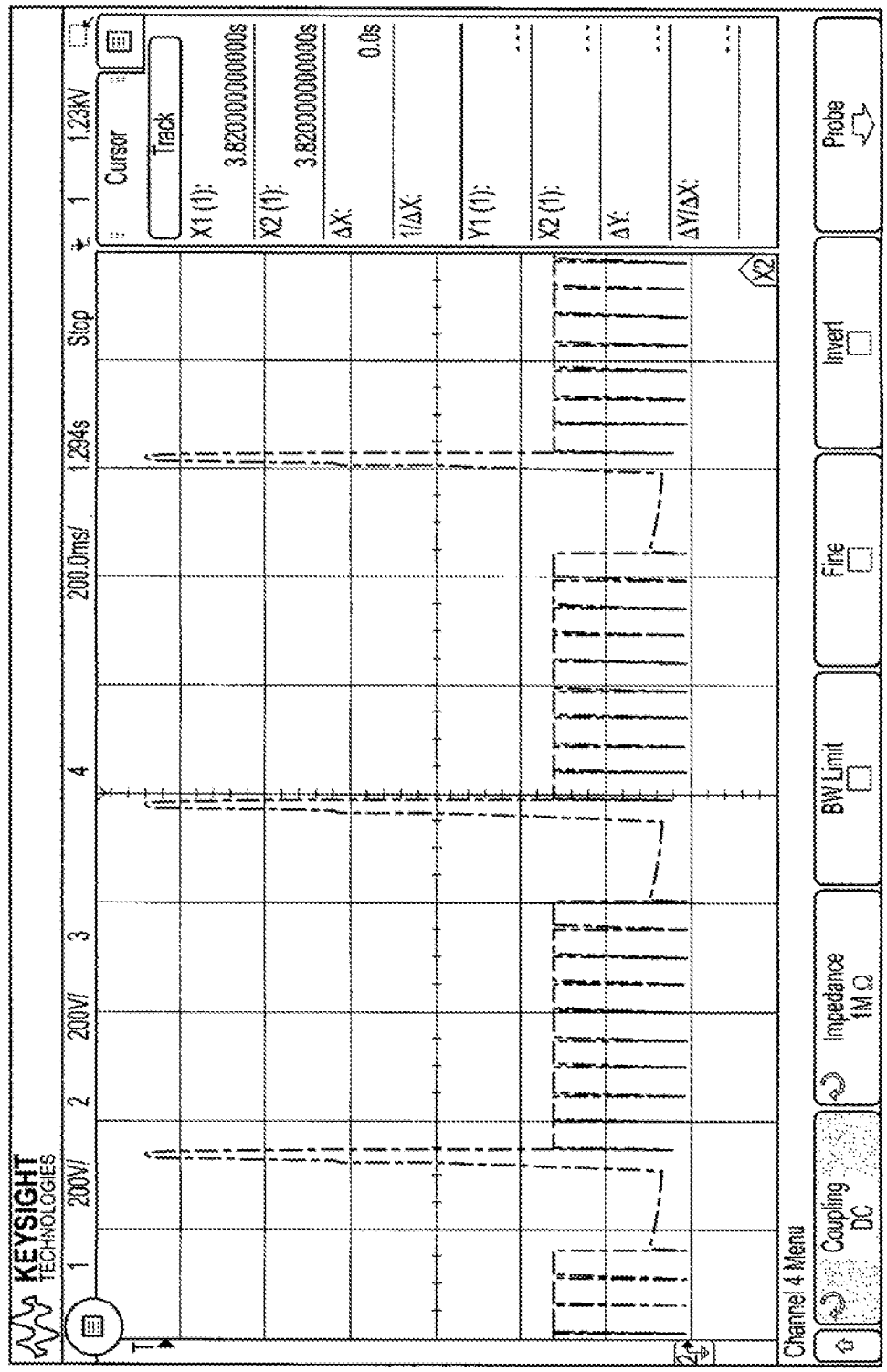
FIG. 9 shows adjusted pulses applied at a lower voltage level while still delivering a sufficient energy level, under an embodiment.

FIG. 9 shows a scope trace that illustrates this particular action. The first pulse of each pulse train is applied at a high voltage level. The system determines, based on skin resistance, that skin breakdown has occurred. Therefore, the subsequent pulses are applied at a lower voltage level while still delivering an adequate energy level. The efficacy of each pulse is monitored. If any pulse is determined to be ineffective, the developed voltage can be returned to a high enough level to cause breakdown.

Figure 10:
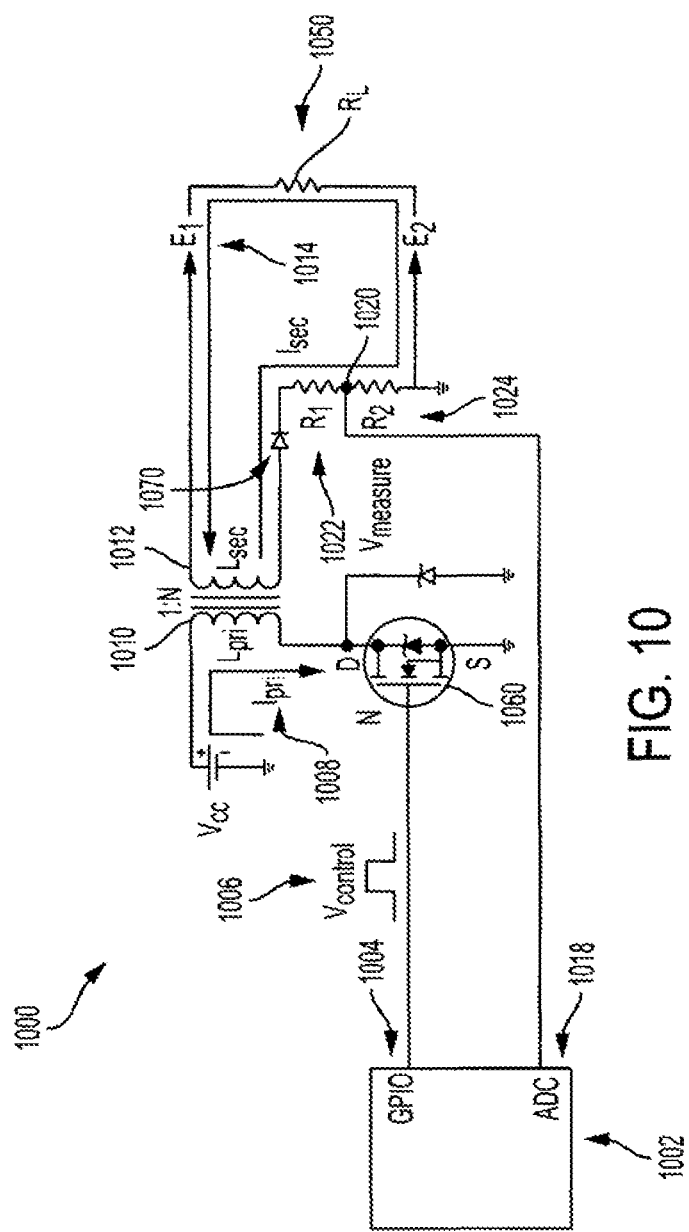
FIG. 10 shows a circuit for measuring intensity of an electrical stimulation, under an embodiment.

An alternative method and apparatus for measuring the intensity of electrical stimulus delivered to an animal is described below. FIG. 10 shows a microcontroller 1002 driving current/voltage to circuit 1000. The circuit delivers an electrical stimulus to an animal wearing a collar housing the circuit. The circuit delivers the stimulus at resistor 1050 ($R_L$) which models the resistive load presented to the circuit (i.e., $R_L$ is a model for the skin of the animal wearing the collar).

A method of measuring the intensity of the stimulus delivered at resistor 1050 ($R_L$) is described herein. The method includes setting the general purpose input/output (GPIO) 1004 pin to high. A one shot timer with interrupt on time out is configured to maintain the high position for the desired pulse width. The one shot timer works something like an alarm clock. A timer may be set to "go on" at some point in time (i.e., at time $t_0$=0 under this example) and then "go off" after a certain period of time (i.e., at $t_1$ under this example). During the configured pulse width, the microcontroller 1002 provides a control voltage 1006 ($V_{control}$) which allows primary current 1008 ($I_{pri}$) to flow. (Note that the transistor 1060 functions as a switch, i.e. the transistor allows primary current 1008 ($I_{pri}$) to flow when control voltage 1006 ($V_{control}$) is applied). The primary current 1008 ($I_{pri}$) flows through primary winding 1010 ($L_{pri}$). No current flows through the secondary 1012 ($L_{sec}$) during this time due to the direction of diode 1070. Therefore, primary current results in energy being stored in the magnetic core of the transformer. The transformer comprises primary to secondary winding ratio of 1:N. Secondary current will be induced to flow as a result of a flyback phase reversal when the primary current is stopped by the removal of the control signal at transistor 1060. The secondary current 1014 ($I_{sec}$) provides a voltage drop across resistor 1050 ($R_L$), i.e. power dissipation at $R_L$ or delivery of stimulus to the animal.

In the timer interrupt service routine, the microcontroller 1002 returns the GPIO 1004 to low. Immediately following this instruction, the microcontroller 1002 triggers the analog to digital converter 1018 to sample voltage ($V_{measure}$) at location 1020 between resistor 1022 ($R_1$) and resistor 1024 ($R_2$).

As indicated above, the microcontroller sets GPIO 1004 to high. FIG. 11A shows a one shot timer with interrupt for desired pulse width $t_1$. The microcontroller shuts the GPIO 1004 off, i.e. returns it to low, at time $t_1$. The microcontroller then triggers the ADC to sample voltage ($V_{measure}$) of the circuit at location 1020 at $t_1$. It will take a small amount of time for the microcontroller and its ADC to initiate and complete the conversion, therefore the ADC sample ($V_{measure}$) occurs at a time $t_2$ which is slightly greater than $t_1$.

FIG. 11B shows primary current ($I_{pri}$) as a function of time during the configured one shot pulse width. FIG. 11C shows secondary current ($I_{sec}$) as a function of time after time $t_1$, i.e. after the microcontroller returns GPIO 1004 to low. When the flow of primary current ($I_{pri}$) terminates after $t_1$, note that secondary current ($I_{sec}$) experiences exponential decay to zero.

FIG. 11D shows sample voltage $V_{measure}$ over time. Of course, the decay characteristics of $V_{measure}(t)$ correspond to the decay characteristics of $I_{sec}$ as shown in FIG. 11C. In an ADC interrupt service routine, microcontroller 1002 reads and saves an ADC measurement of voltage at location 1020 and at time $t_2$ (described previously), i.e. the ADC measures $V_{measure}(t_2)$. A one-shot timer is configured with interrupt on timeout for desired width $t_3-t_2$. In a timer interrupt service routine, the microcontroller 1002 reads and saves an ADC measurement of voltage at location 1020 and at time $t_3$, i.e. the ADC measures $V_{measure}(t_3)$.

In computing intensity values, the following relationships and equations are important:

$$\text{Peak Primary Current: } I_{pri-pk} = \frac{V_{cc}}{L_{pri}} * t_1$$

$$\text{Peak Secondary Current: } I_{sec-pk} = I_{pri-pk}/N$$

$$\text{Voltage Measurement: } V_{measure}(t) = R_2 * I_{sec-pk} * e^{-(t-t_1)/Tc}$$

Intensity level may be computed as follows:

$$\text{Intensity} = I_{sec}(t) * \text{Effective Duration}$$

$$\text{Intensity} = I_{sec-pk} * 3Tc$$

$$T_c = L_{sec}/(R_1+R_2+R_L)$$

The method described herein uses $V_{measure}(t_2)$, $V_{measure}(t_3)$, $t_2$, $t_3$, $R_2$, and Tc to compute intensity of electrical stimulus delivered by circuit 1000.

$$\frac{V_{measure}(t_2)}{V_{measure}(t_3)} = \frac{R_2 * I_{sec-pk} * e^{-(t_2-t_1)/Tc}}{R_2 * I_{sec-pk} * e^{-(t_3-t_1)/Tc}} \quad (1)$$

$$\frac{V_{measure}(t_2)}{V_{measure}(t_3)} = \frac{e^{-(t_2-t_1)/Tc}}{e^{-(t_3-t_1)/Tc}} \quad (2)$$

$$\frac{V_{measure}(t_2)}{V_{measure}(t_3)} = e^{-(t_2-t_1)/Tc+(t_3-t_1)/Tc} \quad (3)$$

$$\ln\left(\frac{V_{measure}(t_2)}{V_{measure}(t_3)}\right) = -(t_2-t_1)/Tc + (t_3-t_1)/Tc \quad (4)$$

$$\ln\left(\frac{V_{measure}(t_2)}{V_{measure}(t_3)}\right) = (t_3-t_2)/Tc \quad (5)$$

$$Tc = \frac{(t_3-t_2)}{\ln\left(\frac{V_{measure}(t_2)}{V_{measure}(t_3)}\right)} \quad (6)$$

$$V_{measure}(t_2) = R_2 * I_{sec-pk} * e^{-(t_2-t_1)/Tc} \quad (7)$$

$$V_{measure}(t_2) = R_2 * I_{sec-pk} \quad (8)$$

$$I_{sec-pk} = R_2/V_{measure}(t_2) \quad (9)$$

$$\text{INTENSITY} = I_{sec-pk} * 3Tc \quad (10)$$

Note the equations (6) and (9) provide values necessary to calculate Intensity using equation (10). Note also that equations (6) and (9) are based on voltage measurements ($V_{measure}(t_2)$, $V_{measure}(t_3)$), known time values ($t_2$, $t_3$), known resistor value $R_2$, and known (deduced) time constant value Tc. A feedback control loop may now be employed to provide a nearly constant INTENSITY for variations in Tc. Hence, the device may compensate for changes in $R_L$.

A device is described herein that comprises under one embodiment a microcontroller coupled to a transformer, wherein the transformer comprises a primary winding and a secondary winding, wherein the microcontroller is connected to a secondary circuit at a first location. The microcontroller is configured to provide a voltage at a first value to the primary winding for a first period of time, the providing the voltage for the first period of time including initiating delivery of the voltage at time $t_0$ and ceasing the delivery at time $t_1$, the ceasing the delivery inducing a flow of current through the secondary winding and the secondary circuit, wherein the secondary circuit comprises at least one resistor, at least one diode, and a resistive load, wherein the resistive load is variable. The microcontroller is configured to measure a first voltage at the first location in the secondary circuit at time $t_2$ and to measure a second voltage at the first location at time $t_3$. The microcontroller is configured to compute a time constant of the secondary circuit using a difference between time $t_3$ and time $t_2$, the first measured voltage, and the second measured voltage. The microcontroller is configured to compute a peak current in the secondary circuit using a value of the at least one resistor and the first measured voltage. The microcontroller configured to compute an intensity level at the resistive load using the computed peak current and the time constant of the secondary circuit. The microcontroller is configured to monitor the intensity level, the monitoring the intensity level including iteratively performing the providing a voltage at the first value to the primary winding for the first period of time, the measuring the first voltage and the second voltage, the computing the time constant, the computing the peak current, and the computing the intensity level.

The monitoring the intensity level of an embodiment includes maintaining the intensity level at a near constant value by iteratively adjusting at least one of the first value and the first period of time.

Computer networks suitable for use with the embodiments described herein include local area networks (LAN), wide area networks (WAN), Internet, or other connection services and network variations such as the world wide web, the public internet, a private internet, a private computer network, a public network, a mobile network, a cellular network, a value-added network, and the like. Computing devices coupled or connected to the network may be any microprocessor controlled device that permits access to the network, including terminal devices, such as personal computers, workstations, servers, mini computers, main-frame computers, laptop computers, mobile computers, palm top computers, hand held computers, mobile phones, TV set-top boxes, or combinations thereof. The computer network may include one of more LANs, WANs, Internets, and computers. The computers may serve as servers, clients, or a combination thereof.

The systems and methods for dynamic voltage modulation can be a component of a single system, multiple systems, and/or geographically separate systems. The systems and methods for dynamic voltage modulation can also be a subcomponent or subsystem of a single system, multiple systems, and/or geographically separate systems. The components of systems and methods for dynamic voltage modulation can be coupled to one or more other components (not shown) of a host system or a system coupled to the host system.

One or more components of the systems and methods for dynamic voltage modulation and/or a corresponding interface, system or application to which the systems and methods for dynamic voltage modulation is coupled or connected includes and/or runs under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

The components of any system that include the systems and methods for dynamic voltage modulation can be located together or in separate locations. Communication paths couple the components and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Aspects of the systems and methods for dynamic voltage modulation and corresponding systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the systems and methods for dynamic voltage modulation and corresponding systems and methods include: microcontrollers with memory (such as electronically erasable programmable read only memory (EEPROM)), embedded microprocessors, firmware, software, etc. Furthermore, aspects of the systems and methods for dynamic voltage modulation and corresponding systems and methods may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that any system, method, and/or other components disclosed herein may be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the systems and methods for dynamic voltage modulation is not intended to be exhaustive or to limit the systems and methods to the precise forms disclosed. While specific embodiments of, and examples for, the systems and methods for dynamic voltage modulation and corresponding systems and methods are described herein for illustrative purposes, various equivalent modifications are possible within the scope of the systems and methods, as those skilled in the relevant art will recognize. The teachings of the systems and methods for dynamic voltage modulation and corresponding systems and methods provided herein can be applied to other systems and methods, not only for the systems and methods described above.

The elements and acts of the various embodiments described above can be combined to provide further embodiments. These and other changes can be made to the systems and methods for dynamic voltage modulation and corresponding systems and methods in light of the above detailed description.

I claim:

1. A device comprising,
   a microcontroller coupled to a transformer, wherein the transformer comprises a primary winding and a secondary winding, wherein the microcontroller is connected to a secondary circuit at a first location;
   the microcontroller configured to provide a voltage at a first value to the primary winding for a first period of time, the providing the voltage for the first period of time including initiating delivery of the voltage at time t0 and ceasing the delivery at time t1, the ceasing the delivery inducing a flow of current through the secondary winding and the secondary circuit, wherein the secondary circuit comprises at least one resistor, at least one diode, and a resistive load, wherein the resistive load is variable;
   the microcontroller configured to measure a first voltage at the first location in the secondary circuit at time t2 and to measure a second voltage at the first location at time t3;
   the microcontroller configured to compute a time constant of the secondary circuit using a difference between the time t3 and the time t2, the measured first voltage, and the measured second voltage;
   the microcontroller configured to compute a peak current in the secondary circuit using a value of the at least one resistor and the measured first voltage;
   the microcontroller configured to compute an intensity level at the resistive load using the computed peak current and the time constant of the secondary circuit;
   the microcontroller configured to monitor the intensity level, the monitoring the intensity level including iteratively performing the providing a voltage at the first value to the primary winding for the first period of time, the measuring the first voltage and the second voltage, the computing the time constant, the computing the peak current, and the computing the intensity level,
   wherein the monitoring the intensity level includes maintaining the intensity level at a constant value by iteratively adjusting at least one of the first value and the first period of time.

* * * * *